(12) United States Patent
Chen et al.

(10) Patent No.: US 10,674,945 B2
(45) Date of Patent: Jun. 9, 2020

(54) REAL TIME MODELING OF ANALYTE TRANSPORT IN A MEDIUM SURROUNDING AN IMPLANTED SENSOR TO CALCULATE A CORRESPONDING CONCENTRATION OF ANALYTE IN A DISTANT MEDIUM

(71) Applicant: Senseonics, Incorporated, Germantown, MD (US)

(72) Inventors: Xiaoxiao Chen, Washington, DC (US); Andrew Dehennis, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 147 days.

(21) Appl. No.: 15/715,535

(22) Filed: Sep. 26, 2017

(65) Prior Publication Data
US 2018/0085038 A1    Mar. 29, 2018

Related U.S. Application Data

(60) Provisional application No. 62/400,277, filed on Sep. 27, 2016.

(51) Int. Cl.
*A61B 5/145* (2006.01)
*A61B 5/07* (2006.01)
*A61B 5/00* (2006.01)

(52) U.S. Cl.
CPC ......... *A61B 5/14503* (2013.01); *A61B 5/076* (2013.01); *A61B 5/14532* (2013.01);
(Continued)

(58) Field of Classification Search
CPC ............................ A61B 5/14503; A61B 5/076
(Continued)

(56) References Cited

U.S. PATENT DOCUMENTS 8,073,548 B2    12/2011    Colvin, Jr. et al.
9,414,775 B2     8/2016    Colvin, Jr. et al.
(Continued)

FOREIGN PATENT DOCUMENTS

EP      2 770 907 B1    7/2018

OTHER PUBLICATIONS

Matthew T. Novak et. al., "Modeling the relative impact of capsular tissue effects on implanted glucose sensor time lag and signal attenuation," 398(4) Analytical and Bioanalytical Chemistry 1695-1705 (Oct. 2010).
(Continued)

*Primary Examiner* — Daniel L Cerioni
(74) *Attorney, Agent, or Firm* — Rothwell, Figg, Ernst & Manbeck, P.C.

(57) ABSTRACT

An analyte monitoring system and method. The analyte monitoring system may include an analyte sensor and a transceiver. The analyte sensor may include an indicator element that exhibits one or more detectable properties based on a concentration of an analyte in proximity to the indicator element. The transceiver may be configured to (i) receive measurement information from the analyte sensor, (ii) calculate the concentration of the analyte in proximity to the indicator element based on at least the received measurement information, and (iii) calculate a blood analyte concentration based on the calculated concentration of the analyte in proximity to the indicator element by (1) incorporating the calculated concentration of the analyte in proximity to the indicator element into a governing equation that models analyte transport over an interval, and (2) solving the governing equation. In some embodiments, the governing equation includes no more than two discrete boundary conditions.

13 Claims, 15 Drawing Sheets

(52) U.S. Cl.
CPC .............. *A61B 5/6861* (2013.01); *A61B 5/746* (2013.01); *A61B 5/7455* (2013.01); *A61B 2560/0219* (2013.01); *A61B 2562/0271* (2013.01); *A61B 2562/162* (2013.01)

(58) Field of Classification Search
USPC ........................................................ 600/302
See application file for complete search history.

(56) References Cited

U.S. PATENT DOCUMENTS

| | | |
|---|---|---|
| 9,693,714 B2 | 7/2017 | DeHennis et al. |
| 10,028,686 B2 | 7/2018 | Hayter |
| 2008/0177518 A1* | 7/2008 | Krishnamoorthy ........................ G06F 17/5009 703/9 |
| 2011/0237917 A1 | 9/2011 | Roy et al. |
| 2013/0241745 A1 | 9/2013 | Colvin, Jr. et al. |
| 2013/0245401 A1* | 9/2013 | Estes .................. A61B 5/14532 600/309 |
| 2014/0378791 A1 | 12/2014 | DeHennis et al. |
| 2015/0045641 A1* | 2/2015 | Rule .................... A61B 5/7435 600/347 |
| 2015/0182115 A1* | 7/2015 | DeHennis .............. G16H 40/63 600/316 |
| 2016/0007890 A1 | 1/2016 | Kovatchev et al. |
| 2016/0139043 A1* | 5/2016 | Gulati ................ A61B 5/02416 250/341.1 |

OTHER PUBLICATIONS

Bartlett et al., "Modelling of processes in enzyme electrodes," Biosensors & Bioelectronics, vol. 8, No. 9-10, pp. 451-462 (1993).

* cited by examiner

| | Prior Art | Some Embodiments of the Invention |
|---|---|---|
| Capillary/Blood | $r \to \infty$<br><br>$C(t, r \to \infty) = \varepsilon_{tis} C_p(t)$<br><br>- Concentration "far away" from sensor = concentration in blood stream ($C_p(t)$) | $x = 0$<br><br>- Solve for $C^t_{I,x=0}$ |
| Tissue/Capsule Interface | $\frac{C_{FBC}(r=a+L,t)}{\varepsilon_{FBC}} = \frac{C_{tis}(r=a+L,t)}{\varepsilon_{tis}}$<br><br>$D_{FBC} \frac{\partial C_{FBC}}{\partial r}(r = a + L, t) = D_{tis} \frac{\partial C_{tis}}{\partial r}(r = a + L, t)$<br><br>- Conservation of glucose at interface<br>- Concentration and fluxes are equal | - Not needed in single compartment model |
| Sensor | $D_{FBC} A_{sensor} \frac{\partial C_{FBC}}{\partial r}(r = a, t) = Q_{sensor}$<br><br>$Q_{sensor} = \frac{\alpha \gamma C_{FBC}(r = a, t)}{\varepsilon_{FBC}}$<br><br>- Diffusion in fibrous capsule equal to uptake by sensor | $C^t_{I,x=L_C} = C^t_{sensor}$<br><br>$\frac{\partial C^t_{I,x=L_C}}{\partial x} = 0$<br><br>- Concentration at interface equals concentration read by sensor<br>- No accumulation at interface (flux) |

FIG. 10

REAL TIME MODELING OF ANALYTE TRANSPORT IN A MEDIUM SURROUNDING AN IMPLANTED SENSOR TO CALCULATE A CORRESPONDING CONCENTRATION OF ANALYTE IN A DISTANT MEDIUM

CROSS-REFERENCE TO RELATED APPLICATION

The present application claims the benefit of priority to U.S. Provisional Application Ser. No. 62/400,277, filed on Sep. 27, 2016, which is incorporated herein by reference in its entirety.

BACKGROUND

Field of Invention

Aspects of the present invention relate to a transceiver utilizing measurement data obtained by a sensor to calculate a concentration of analyte in close proximity to the sensor and calculating a corresponding concentration of the analyte in a distant medium, e.g., a bloodstream.

Discussion of the Background

Conventional analyte (e.g., glucose) monitoring systems typically comprise a sensor partially or fully implanted in the body of an animal (e.g., a human). These sensors detect the concentration of the analyte in close proximity to the sensor based on one or more detectable properties of the analyte. These sensors are typically implanted, fully or partially in subcutaneous tissue of the animal. The analyte concentration values calculated by the analyte monitoring systems will thus reflect the analyte concentration of the surrounding medium, e.g., an interstitial fluid space or fibrous capsule surrounding the sensor. However, a typical use of these monitoring systems may be to monitor the concentration of the analyte in a distant medium (e.g., monitoring blood glucose concentration in a diabetic patient). These measurements must be precise in these applications, as therapeutic decisions may be made by a patient or their healthcare provider based upon these measurements. However, the concentration of the analyte in close proximity to the sensor will often "lag" behind the concentration of the analyte in the distant medium, e.g., a bloodstream, as the analyte must diffuse through the surrounding medium, e.g., the interstitial fluid space or fibrous capsule surrounding the sensor. In the body of an animal, e.g., a human, the analyte (e.g., glucose) may be metabolized by other cells as it diffuses through the medium surrounding the sensor, and the surrounding tissue may react to the implanted sensor by encapsulating it, e.g., in a fibrous capsule. See Matthew T. Novak et. al., *Modeling the relative impact of capsular tissue effects on implanted glucose sensor time lag and signal attenuation*, 398(4) Analytical and Bioanalytical Chemistry 1695 (October 2010). These further complicate a correlation between the measured analyte concentration and the corresponding concentration in the distant medium. Id.

The current state of the art corrects for this "lag" by modeling the transport of the analyte as a two-compartment, unidimensional diffusion-reaction problem. Id. However, this approach is limited in several aspects. The state of the art utilizes two governing equations, one for each "compartment" over which the transport of the analyte is modeled. Additionally, four boundary conditions and several parameters are necessary to numerically approximate a solution. Id. The excessive definitions and equations utilized make the current model difficult to implement in a real-time system, as a numerical solution would require excessive computing power or memory to accomplish. A simpler, yet robust, approach is necessary to implement the calculation of the analyte concentration in the distant medium in real time while providing the necessary precision for use in a diagnostic setting.

SUMMARY

A device (e.g. an analyte sensor) may be implanted (fully or partially) in a body (e.g. a human body) in order to measure the concentration of an analyte (e.g. glucose) by measuring one or more detectable properties of the analyte in close proximity to the device. The manner in which an analyte (e.g., glucose) diffuses across a medium (e.g. an interstitial fluid space) surrounding the device from a distant medium (e.g. a bloodstream) may vary widely depending on several factors, such as, for example, the length of a fibrous capsule that may encapsulate the device. Because this transport may vary widely, and because the device may only directly measure one or more detectable properties of the analyte in close proximity to the device, the corresponding concentration of the analyte in the distant medium may differ greatly than what is determined based on the measurements taken by the device. Aspects of the invention may utilize the measurements taken by the device and model the transport of the analyte of interest across a medium in order to calculate a corresponding concentration of the analyte in the distant medium.

One aspect of the invention may provide an analyte monitoring system that includes an analyte sensor and a transceiver. The analyte sensor may include an indicator element that exhibits one or more detectable properties based on an amount or concentration of an analyte in proximity to the indicator element, The transceiver may be configured to (i) receive measurement information from the analyte sensor, (ii) calculate the concentration of the analyte in proximity to the indicator element based on at least the received measurement information, and (iii) calculate a blood analyte concentration based on the calculated concentration of the analyte in proximity to the indicator element by (1) incorporating the calculated concentration of the analyte in proximity to the indicator element into a governing equation that models analyte transport over an interval, and (2) solving the governing equation. The governing equation may include no more than two discrete boundary conditions.

Another aspect of the invention may provide a method. The method may include receiving measurement information from an analyte sensor. The analyte sensor may include an indicator element that exhibits one or more detectable properties based on an amount or concentration of an analyte in proximity to the indicator element. The method may include calculating the concentration of the analyte in proximity to the indicator element based on at least the received measurement information. The method may also include calculating a blood analyte concentration based on the calculated concentration of the analyte in proximity to the indicator element by (1) incorporating the calculated concentration of the analyte in proximity to the indicator element into a governing equation that modely analyte transport from a bloodstream across a medium surrounding the analyte sensor and (2) solving the governing equation. The governing equation may include no more than two discrete boundary conditions.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIG. 10 is a chart contrasting exemplary boundary conditions utilized in some embodiments of the present invention and an exemplary prior art model.

DETAILED DESCRIPTION OF PREFERRED EMBODIMENTS

Figure 1:
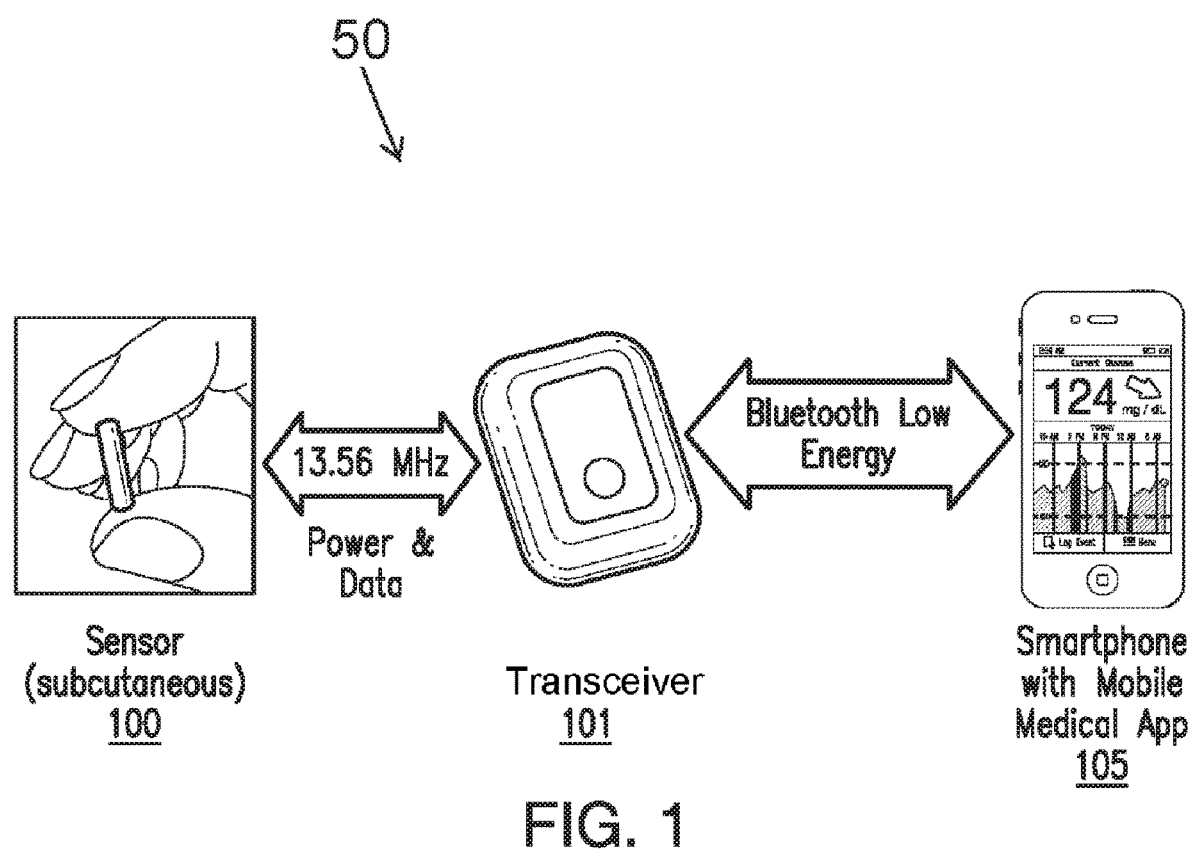
FIG. 1 is a schematic view illustrating a sensor and transceiver of an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some embodiments, the analyte monitoring system 50 may include one or more of an analyte sensor 100, a transceiver 101, and a display device 105. In some embodiments, the sensor 100 may be small, fully subcutaneously implantable sensor measures analyte (e.g., glucose) concentrations in a medium (e.g., interstitial fluid space 608) of a living animal (e.g., a living human). However, this is not required, and, in some alternative embodiments, the sensor 100 may be a partially implantable (e.g., transcutaneous) sensor or a fully external sensor. In some embodiments, the transceiver 101 may be an externally worn transceiver (e.g., attached via an armband, wristband, waistband, or adhesive patch). In some embodiments, the transceiver 101 may remotely power and/or communicate with the sensor to initiate and receive the measurements (e.g., via near field communication (NFC)). However, this is not required, and, in some alternative embodiments, the transceiver 101 may power and/or communicate with the sensor 100 via one or more wired connections. In some non-limiting embodiments, the transceiver 101 may be a smartphone (e.g., an NFC-enabled smartphone). In some embodiments, the transceiver 101 may communicate information (e.g., one or more analyte concentrations) wirelessly (e.g., via a Bluetooth™ communication standard such as, for example and without limitation Bluetooth Low Energy) to a hand held application running on a display device 105 (e.g., smartphone). In some embodiments, information can be downloaded from the transceiver 101 through a Universal Serial Bus (USB) port. In some embodiments, the analyte monitoring system 50 may include a web interface for plotting and sharing of uploaded data.

Figure 2:
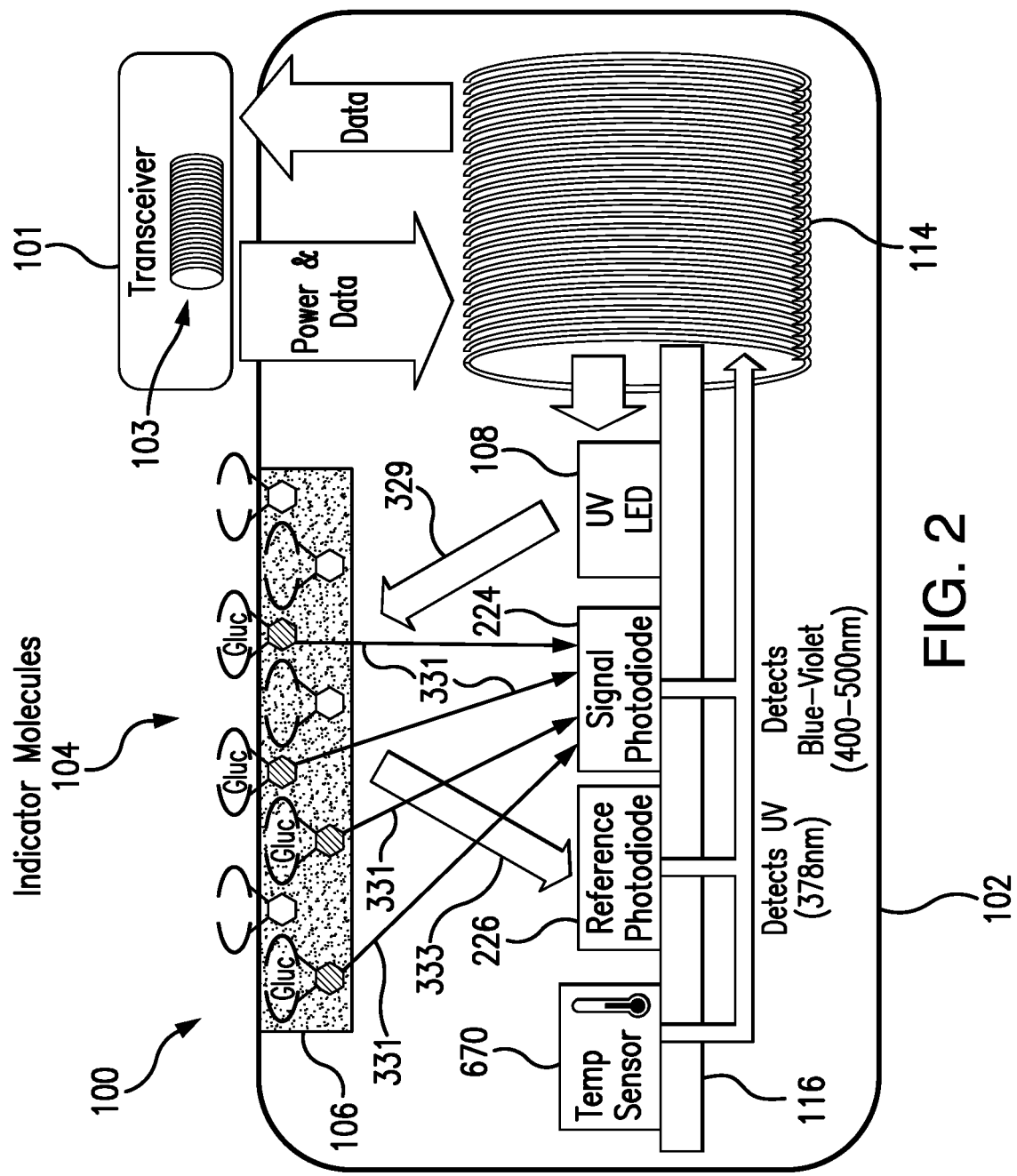
FIG. 2 is a schematic view illustrating a sensor and transceiver of an analyte monitoring system embodying aspects of the present invention.

In some embodiments, as illustrated in FIG. 2, the transceiver 101 may include an inductive element 103, such as, for example, a coil. The transceiver 101 may generate an electromagnetic wave or electrodynamic field (e.g., by using a coil) to induce a current in an inductive element 114 of the sensor 100, which powers the sensor 100. The transceiver 101 may also convey data (e.g., commands) to the sensor 100. For example, in a non-limiting embodiment, the transceiver 101 may convey data by modulating the electromagnetic wave used to power the sensor 100 (e.g., by modulating the current flowing through a coil 103 of the transceiver 101). The modulation in the electromagnetic wave generated by the transceiver 101 may be detected/extracted by the sensor 100. Moreover, the transceiver 101 may receive data (e.g., measurement information) from the sensor 100. For example, in a non-limiting embodiment, the transceiver 101 may receive data by detecting modulations in the electromagnetic wave generated by the sensor 100, e.g., by detecting modulations in the current flowing through the coil 103 of the transceiver 101.

The inductive element 103 of the transceiver 101 and the inductive element 114 of the sensor 100 may be in any configuration that permits adequate field strength to be achieved when the two inductive elements are brought within adequate physical proximity.

In some non-limiting embodiments, as illustrated in FIG. 2, the sensor 100 may be encased in a sensor housing 102 (i.e., body, shell, capsule, or encasement), which may be rigid and biocompatible. The sensor 100 may include an analyte indicator element 106, such as, for example, a polymer graft coated, diffused, adhered, or embedded on or in at least a portion of the exterior surface of the sensor housing 102. The analyte indicator element 106 (e.g., polymer graft) of the sensor 100 may include indicator molecules 104 (e.g., fluorescent indicator molecules) exhibiting one or more detectable properties (e.g., optical properties) based on the amount or concentration of the analyte in proximity to the analyte indicator element 106. In some embodiments, the sensor 100 may include a light source 108 that emits excitation light 329 over a range of wavelengths that interact with the indicator molecules 104. The sensor 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto that is indicative of the level of emission light 331 of the indicator molecules and, thus, the amount of analyte of interest (e.g., glucose). In some non-limiting embodiments, one or more of the photodetectors (e.g., photodetector 226) may be sensitive to excitation light 329 that is reflected from the analyte indicator element 106 as reflection light 333. In some non-limiting embodiments, one or more of the photodetectors may be covered by one or more filters (e.g., bandpass filter 112 of FIG. 6) that allow only a certain subset of wavelengths of light to pass through (e.g., a subset of wavelengths corresponding to emission light 331 or a subset of wavelengths corresponding to reflection light 333) and reflect the remaining wavelengths. In some non-limiting embodiments, the sensor 100 may include a temperature transducer 670. In some non-limiting embodiments, the sensor 100 may include a drug-eluting polymer matrix that disperses one or more therapeutic agents (e.g., an anti-inflammatory drug).

In some embodiments, as illustrated in FIG. 2, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry is secured to the semiconductor substrate 116 and/or a core (e.g., ferrite core) for the inductive element 114. In some embodiments, the semiconductor substrate 116 and/or a core may provide communication paths between the various secured components.

In some embodiments, the one or more of the sensor housing 102, analyte indicator element 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transceiver 101 may be as described in one or more of U.S. application Ser. Nos. 13/761,839, 13/937,871, and 13/650,016.

Although in some embodiments, as illustrated in FIG. 2, the sensor 100 may be an optical sensor, this is not required, and, in one or more alternative embodiments, sensor 100 may be a different type of analyte sensor, such as, for example, an electrochemical sensor, a diffusion sensor, or a pressure sensor. Also, although in some embodiments, as illustrated in FIGS. 1 and 2, the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating using inductive elements 103 and 114, the sensor 100 and transceiver 101 may communicate using one or more wires connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

In some embodiments, the sensor 100 may include a transceiver interface device. In some embodiments where the sensor 100 includes an antenna (e.g., inductive element 114), the transceiver interface device may include the antenna (e.g., inductive element 114) of sensor 100. In some of the transcutaneous embodiments where there exists a wired connection between the sensor 100 and the transceiver 101, the transceiver interface device may include the wired connection.

Figure 3:
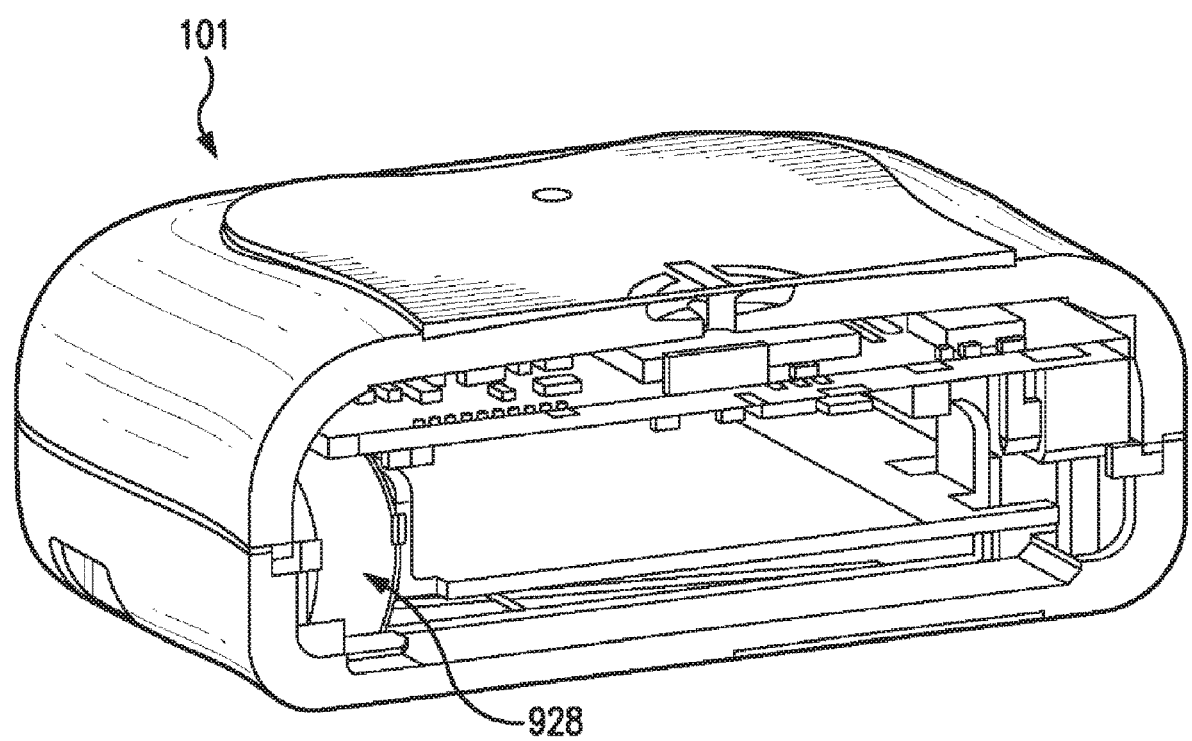
FIG. 3 is a cross-sectional, perspective view of a transceiver embodying aspects of the invention.
Figure 4:
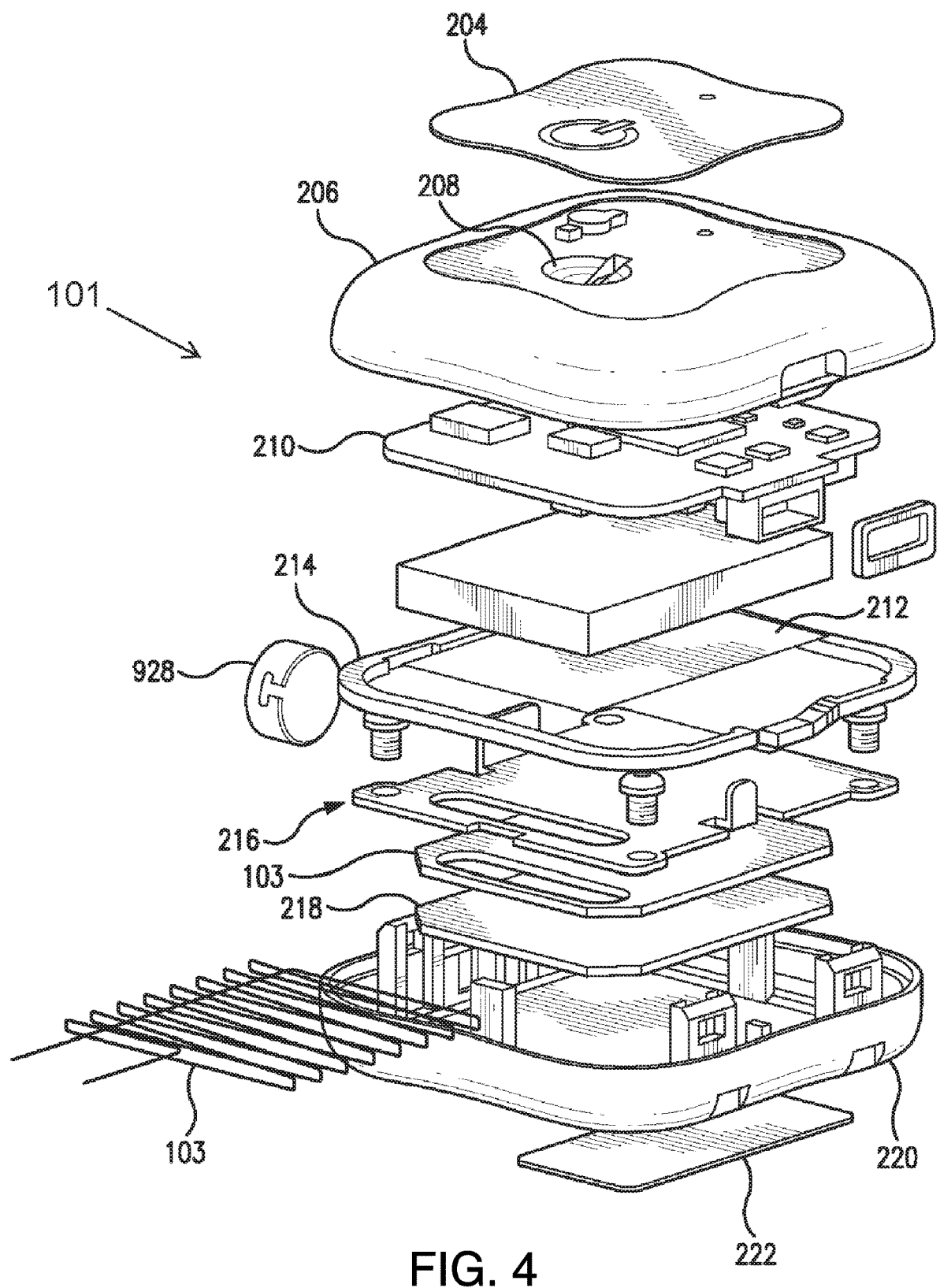
FIG. 4 is an exploded, perspective view of a transceiver embodying aspects of the invention.

FIGS. 3 and 4 are cross-sectional and exploded views, respectively, of a non-limiting embodiment of the transceiver 101, which may be included in the analyte monitoring system illustrated in FIG. 1. As illustrated in FIG. 4, in some non-limiting embodiments, the transceiver 101 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some non-limiting embodiments, the vibration motor 928 may be attached to the front housing 206 or back housing 220 such that the battery 212 does not dampen the vibration of vibration motor 928. In a non-limiting embodiment, the transceiver electronics may be assembled using standard surface mount device (SMD) reflow and solder techniques. In one embodiment, the electronics and peripherals may be put into a snap together housing design in which the front housing 206 and back housing 220 may be snapped together. In some embodiments, the full assembly process may be performed at a single external electronics house. However, this is not required, and, in alternative embodiments, the transceiver assembly process may be performed at one or more electronics houses, which may be internal, external, or a combination thereof. In some embodiments, the assembled transceiver 101 may be programmed and functionally tested. In some embodiments, assembled transceivers 101 may be packaged into their final shipping containers and be ready for sale.

In some embodiments, as illustrated in FIGS. 3 and 4, the antenna 103 may be contained within the housing 206 and 220 of the transceiver 101. In some embodiments, the antenna 103 in the transceiver 101 may be small and/or flat so that the antenna 103 fits within the housing 206 and 220 of a small, lightweight transceiver 101. In some embodiments, the antenna 103 may be robust and capable of resisting various impacts. In some embodiments, the transceiver 101 may be suitable for placement, for example, on an abdomen area, upper-arm, wrist, or thigh of a patient body. In some non-limiting embodiments, the transceiver 101 may be suitable for attachment to a patient body by means of a biocompatible patch. Although, in some embodiments, the antenna 103 may be contained within the housing 206 and 220 of the transceiver 101, this is not required, and, in some alternative embodiments, a portion or all of the antenna 103 may be located external to the transceiver housing. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 5:
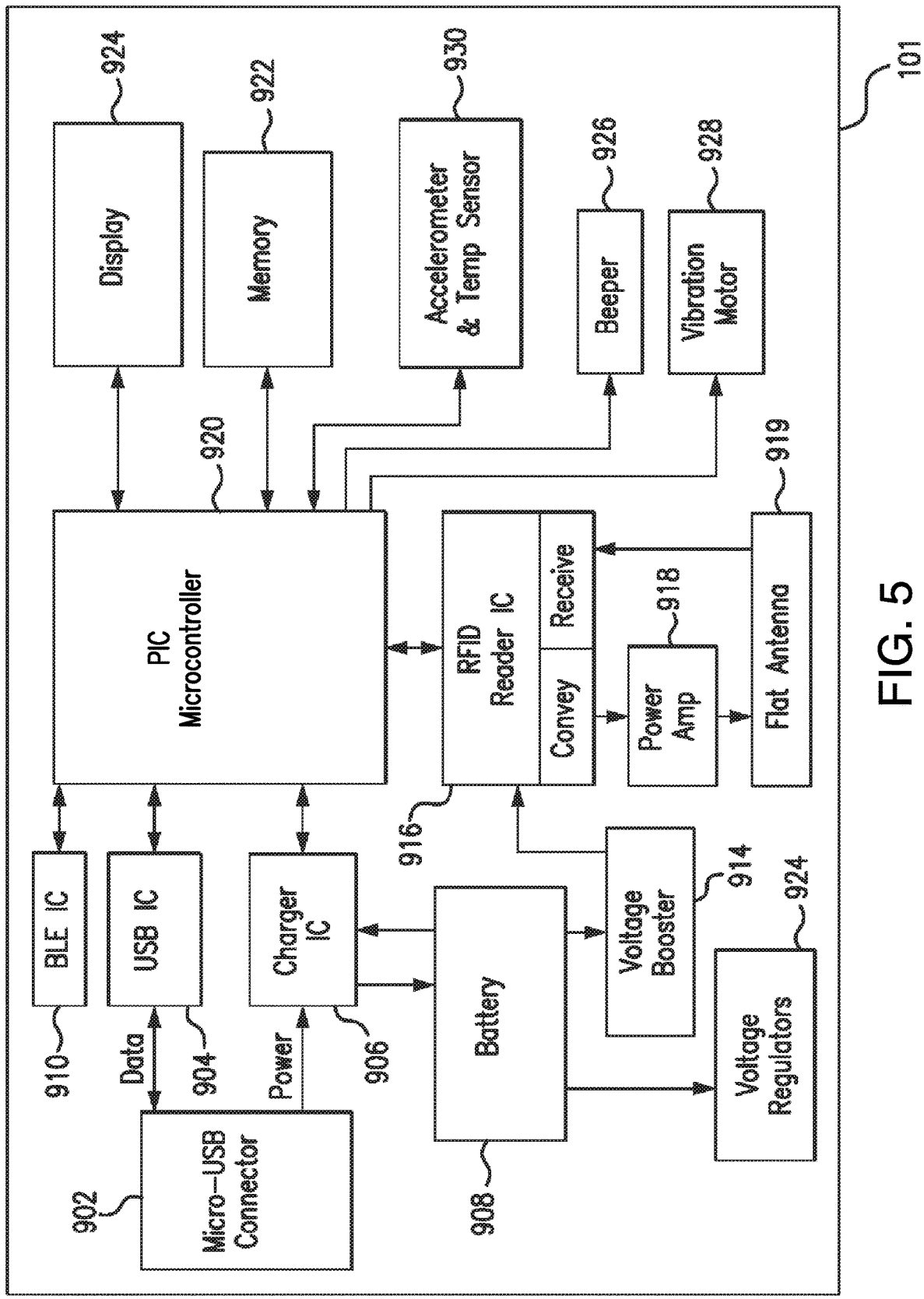
FIG. 5 is a schematic view illustrating a transceiver embodying aspects of the present invention.

FIG. 5 is a schematic view of an external transceiver 101 according to a non-limiting embodiment. In some embodiments, the transceiver 101 may have a connector 902, such as, for example, a Micro-Universal Serial Bus (USB) connector. The connector 902 may enable a wired connection to an external device, such as a personal computer (e.g., personal computer 109) or a display device 105 (e.g., a smartphone).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer (e.g., personal computer 109) or a display device 105 (e.g., a smartphone) and/or to receive power, which may be used, for example, to charge the battery 908.

In some embodiments, the transceiver 101 may have a wireless communication IC 910, which enables wireless communication with an external device, such as, for example, one or more personal computers (e.g., personal computer 109) or one or more display devices 105 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth antenna). In some non-limiting embodiments, the antenna of the wireless communication IC 910 may be entirely contained within the housing (e.g., housing 206 and 220) of the transceiver 101. However, this is not required, and, in alternative embodiments, all or a portion of the antenna of the wireless communication IC 910 may be external to the transceiver housing.

In some embodiments, the transceiver 101 may include a display interface device, which may enable communication by the transceiver 101 with one or more display devices 105. In some embodiments, the display interface device may include the antenna of the wireless communication IC 910 and/or the connector 902. In some non-limiting embodiments, the display interface device may additionally include the wireless communication IC 910 and/or the connector IC 904.

In some embodiments, the transceiver 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some non-limiting embodiments, the sensor 100 and transceiver 101 may communicate using near field communication (NFC) (e.g., at a frequency of 13.56 MHz). In the illustrated embodiment, the inductive element 103 is a flat antenna. In some non-limiting embodiments, the antenna may be flexible. However, as noted above, the inductive element 103 of the transceiver 101 may be in any configuration that permits adequate field strength to be achieved when brought within adequate physical proximity to the inductive element 114 of the sensor 100. In some embodiments, the transceiver 101 may include a power amplifier 918 to amplify the signal to be conveyed by the inductive element 103 to the sensor 100.

The transceiver 101 may include a peripheral interface controller (PIC) microcontroller 920 and memory 922 (e.g., Flash memory), which may be non-volatile and/or capable of being electronically erased and/or rewritten. In some non-limiting embodiments, a portion of the memory 922 may be dedicated to the storage of an analyte transport model. In some non-limiting embodiments, the analyte transport model may contain one governing equation and two boundary conditions, as well as several parameters (e.g. a maximum diffusivity of an analyte). In some non-limiting embodiments, the model may be encoded into memory 922 using one or more standard functions of a programming language such as, for example and without limitation, the C programming language. However, this is not required, and, in some alternative embodiments, the model may be encoded in any format that will permit a real-time solution of the governing equation to be obtained.

In some embodiments, the PIC microcontroller 920 may control the overall operation of the transceiver 101. For example, the PIC microcontroller 920 may control the connector IC 904 or wireless communication IC 910 to transmit data via wired or wireless communication and/or control the RFID reader IC 916 to convey data via the inductive element 103. The PIC microcontroller 920 may also control processing of data received via the inductive element 103, connector 902, or wireless communication IC 910.

In some embodiments, the transceiver 101 may include a sensor interface device, which may enable communication by the transceiver 101 with a sensor 100. In some embodiments, the sensor interface device may include the inductive element 103. In some non-limiting embodiments, the sensor interface device may additionally include the RFID reader IC 916 and/or the power amplifier 918. However, in some alternative embodiments where there exists a wired connection between the sensor 100 and the transceiver 101 (e.g., transcutaneous embodiments), the sensor interface device may include the wired connection.

In some embodiments, the transceiver 101 may include a display 924 (e.g., liquid crystal display and/or one or more light emitting diodes), which PIC microcontroller 920 may control to display data (e.g., analyte concentration values). In some embodiments, the transceiver 101 may include a speaker 926 (e.g., a beeper) and/or vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or temperature sensor, and the additional sensors 930 may be used in the processing performed by the PIC microcontroller 920.

In some embodiments, the transceiver 101 may be a body-worn transmitter that is a rechargeable, external device worn over the sensor implantation or insertion site. The transceiver 101 may supply power to the proximate sensor 100, calculate analyte concentrations from data received from the sensor 100, and/or transmit the calculated analyte concentrations to a display device 105 (see FIG. 1). Power may be supplied to the sensor 100 through an inductive link (e.g., an inductive link of 13.56 MHz). In some embodiments, the transceiver 101 may be placed using an adhesive patch or a specially designed strap or belt. The external transceiver 101 may read measured analyte data from a subcutaneous sensor 100 (e.g., up to a depth of 2 cm or more). The transceiver 101 may periodically (e.g., every 2, 5, or 10 minutes) read sensor data and calculate an analyte concentration and an analyte concentration trend. From this information, the transceiver 101 may also determine if an alert and/or alarm condition exists, which may be signaled to the user (e.g., through vibration by vibration motor 928 and/or an LED of the transmitter's display 924 and/or a display of a display device 105). The information from the transceiver 101 (e.g., calculated analyte concentrations, calculated analyte concentration trends, alerts, alarms, and/or notifications) may be transmitted to a display device 105 (e.g., via Bluetooth Low Energy with Advanced Encryption Standard (AES)-Counter CBC-MAC (CCM) encryption) for display by a mobile medical application (MMA) being executed by the display device 105. In some non-limiting embodiments, the MMA may provide alarms, alerts, and/or notifications in addition to any alerts, alarms, and/or notifications received from the transceiver 101. In one embodiment, the MMA may be configured to provide push notifications. In some embodiments, the transceiver 101 may have a power button (e.g., button 208) to allow the user to turn the device on or off, reset the device, or check the remaining battery life. In some embodiments, the transceiver 101 may have a button, which may be the same button as a power button or an additional button, to suppress one or more user notification signals (e.g., vibration, visual, and/or audible) of the transceiver 101 generated by the transceiver 101 in response to detection of an alert or alarm condition.

In some embodiments, the transceiver 101 of the analyte monitoring system 50 receives raw signals indicative of an amount or concentration of an analyte in proximity to the analyte indicator element 106 of the analyte sensor 100. In some embodiments, the transceiver 101 may receive the raw signals from the sensor 100 periodically (e.g., every 5, 10, or 20 minutes). In some embodiments, the transceiver 101 may receive the raw signals from the sensor 100 continuously. In some embodiments, the raw signals may include one or more analyte measurements (e.g., one or more measurements indicative of the level of emission light 331 from the indicator molecules 104 as measured by the photodetector 224) and/or one or more temperature measurements (e.g., as measured by the temperature transducer 670). In some embodiments, the transceiver 101 may use the received raw signals to calculate analyte concentration in the medium surrounding the sensor 100 (e.g., the interstitial fluid of a human being). In some embodiments, the transceiver 100 may store one or more calculated analyte concentrations (e.g., in memory 922). The transceiver 100 may store these calculated analyte concentrations as a variable (e.g., $C_{sensor}^t$). In some embodiments, the transceiver 100 may convey one or more calculated analyte concentrations to the display device 105.

Figure 6:
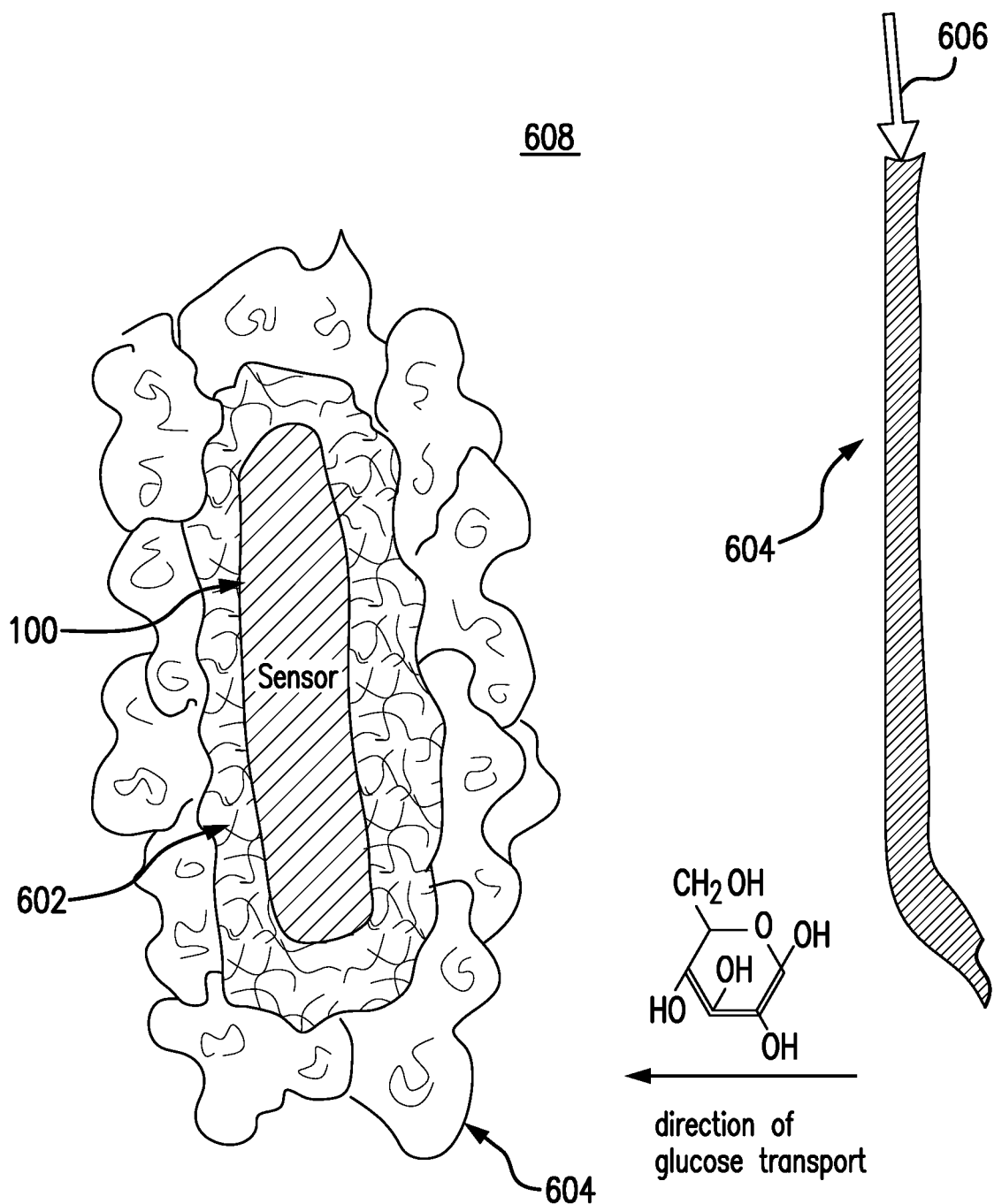
FIG. 6 is a graphical depiction of an exemplary medium that may surround an analyte monitoring sensor embodying aspects of the present invention.
Figure 7:
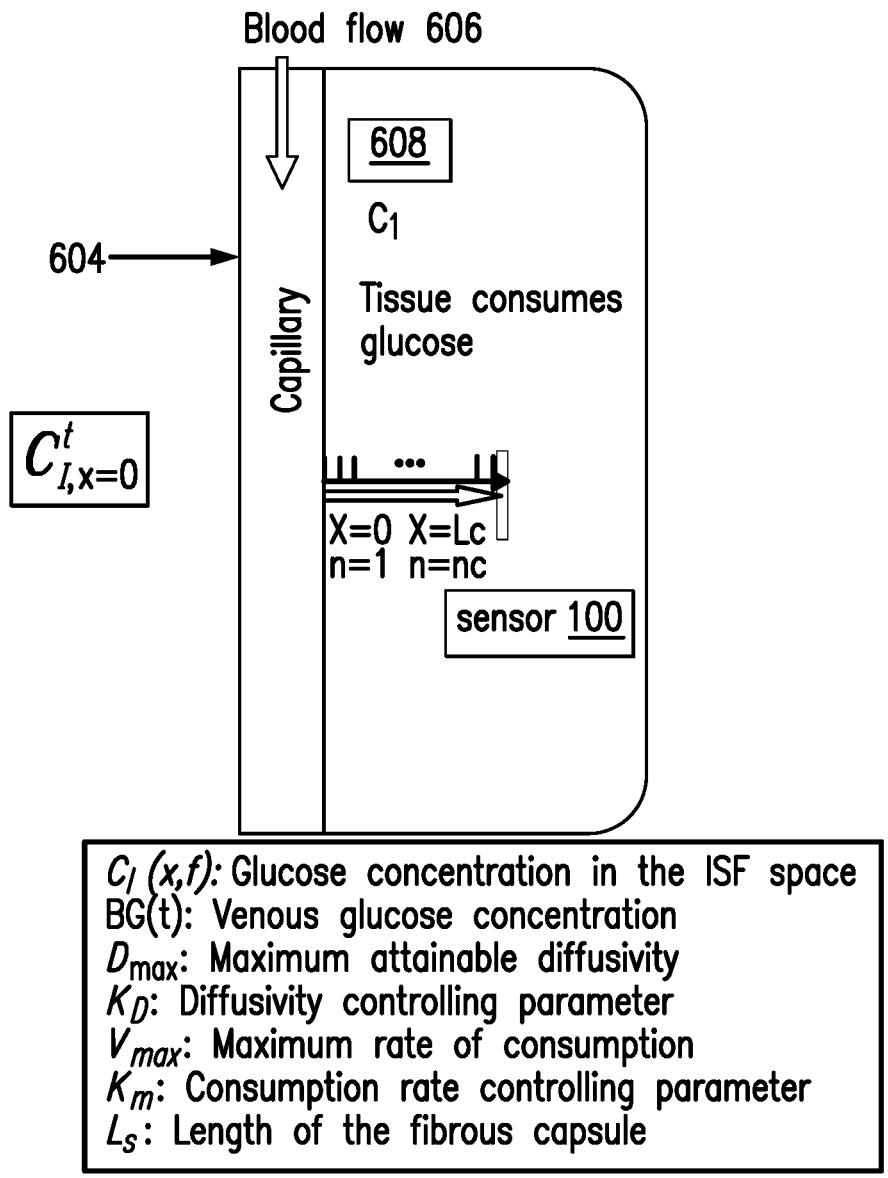
FIG. 7 is a graphical depiction of an exemplary interval over which the concentration of an analyte is modeled in some embodiments of the present invention.
Figure 8:
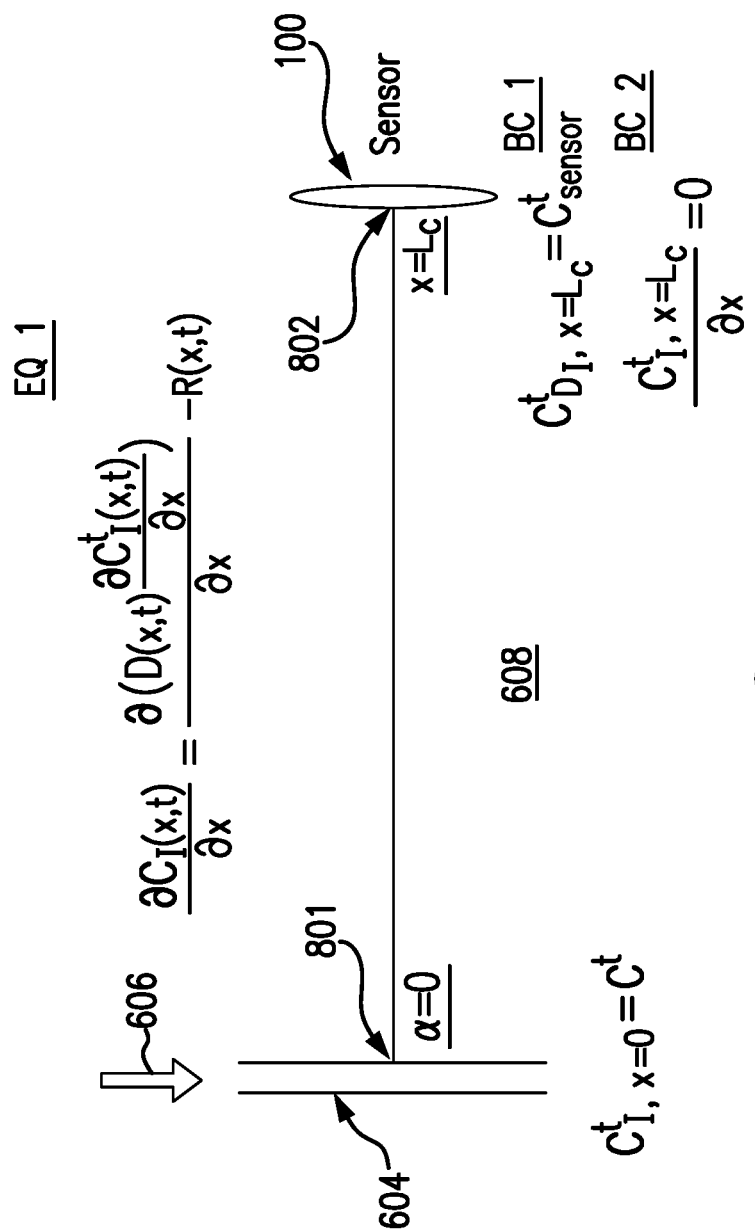
FIG. 8 is a simplified graphical depiction of an exemplary interval over which the concentration of an analyte is modeled in some embodiments of the present invention with exemplary equations and boundary conditions included.

FIGS. 6 and 7 illustrate graphical depictions of an exemplary medium that may surround an analyte monitoring sensor and an exemplary interval over which the concentration of an analyte is modeled according to some non-limiting embodiments of the present invention. FIG. 8 is a simplified graphical depiction of an exemplary interval over which the concentration of an analyte is modeled in some embodiments of the present invention with exemplary equations and boundary conditions included. In some embodiments, as shown in FIG. 6, a fibrous capsule 602 may encapsulate the sensor 100. In some embodiments, the analyte monitoring system 50 may store one or more values (e.g., in memory 922) that correspond to the locations of endpoints. In some embodiments, the one or more stored values may be based on theoretical or empirical knowledge or obtained or estimated through in vivo sensor data. In some embodiments, the one or more stored values may be dependent on the location of the implanted sensor within the patient. In some embodiments, $L_c$ may relate to the density of the tissue. In some embodiments, as shown in FIG. 8, a first endpoint 801 may be defined with a numerical value (e.g., 0). This endpoint may correspond to the interface between two media, e.g., the interface between a capillary 604 through which blood 606 flows and interstitial fluid 608 of a living human being. In some embodiments, as shown in FIG. 8, a second endpoint 802 may be defined numerically, for example, as the absolute value of the distance between the first and second endpoints 801 and 802. In some embodiments, any distance units may be used so long as the definition of the two endpoints 801 and 802 results in a closed and defined interval between them. In some embodiments, the second endpoint 802 may be defined as the location of the sensor 100 (e.g., the interface between the sensor 100 and the surrounding interstitial fluid 608 of a living human being).

In some embodiments, the analyte monitoring system 50 may store several parameters (e.g., in memory 922) that may be incorporated into a governing equation, which also may be stored (e.g., in memory 922). In some embodiments, these values may include one or more of $D_{max}$ (maximum attainable diffusivity), $K_D$ (diffusivity controlling parameter), $V_{max}$ (maximum rate of analyte consumption), $K_m$ (consumption rate controlling parameter), and $L_S$ (length of fibrous capsule). Some embodiments may contain additional or fewer parameters than those listed above, which are meant to be exemplary and neither exhaustive nor limiting.

In some embodiments, the analyte monitoring system 50 may calculate in real time the corresponding concentration of an analyte in a medium that is not in immediate proximity to the sensor 100, e.g., a patient's capillary 604. In some embodiments, this concentration may be found by solving a governing equation that is stored in the transceiver 101, e.g., in memory 922. In some non-limiting embodiments, this governing equation may be defined as follows:

$$\frac{\partial C_I(x, t)}{\partial t} = \frac{\partial\left(D(x, t)\frac{\partial C_I(x, t)}{\partial x}\right)}{\partial x} - R(x, t)$$

Where $C_I(x, t)$ is the calculated concentration of analyte at a given location (x) and time (t), D(x, t) is the corresponding diffusivity of the analyte at the same given location and time, and R(x, t) is a term that models the degradation of the analyte, e.g., through the consumption of the analyte by cells in the interstitial fluid 608.

In some non-limiting embodiments, D(x, t) may have the general form of Michaelis-Menten kinetics. In some non-limiting embodiments, for example, D(x, t) may be defined as follows:

$$D(x, t) = \frac{D_{max} * C_I(x, t)}{K_D + C_I(x, t)}$$

In these embodiments, $D_{max}$ may represent the maximum attainable diffusivity of the analyte (e.g., in the interstitial fluid space 608), $K_D$ may represent the diffusivity controlling parameter, and $C_I(x, t)$ may represent the concentration of analyte at a given location (x) and time (t), e.g. in interstitial fluid 608. The above mentioned parameters may be stored in the transceiver 101 in some embodiments, e.g., in memory 922. Some alternative embodiments may have fewer or additional parameters defined, and the equation may be defined in any form that appropriately models a diffusion of the analyte through the medium surrounding the sensor.

In some non-limiting embodiments, R(x, t) may have the general form of Michaelis-Menten kinetics. In some non-limiting embodiments, for example, R(x, t) may be defined as follows:

$$R(x, t) = \frac{V_{max} * C_I(x, t)}{K_m + C_I(x, t)}$$

In these embodiments, $V_{max}$ may represent the maximum rate of degradation of the analyte (e.g., through the consumption by cells in the interstitial fluid space 608), $K_m$ may represent the degradation rate controlling parameter, and $C_I(x, t)$ may represent the concentration of analyte at a given location (x) and time (t), e.g. in interstitial fluid space 608. The above mentioned parameters may be stored in the transceiver 101 in some embodiments, e.g., in memory 922. Some alternative embodiments may have fewer or additional parameters defined, and the equation may be defined in any form that appropriately models a degradation of the analyte in the medium surrounding the sensor.

FIG. 8 mathematically illustrates and defines one non-limiting embodiment of the present invention. In some non-limiting embodiments, the analyte monitoring system 50 may store boundary conditions for the governing equation, e.g., in memory 922. In some embodiments, one boundary condition may be defined as the concentration of analyte at the second endpoint 801 being equal to the calculated concentration of the analyte in proximity to the sensor 100 and another boundary condition is constant flux of the analyte at the second endpoint 801. In some embodiments, these boundary conditions may be defined quantitatively as follows:

$$C_{I,x=L_c}^t = C_{sensor}^t \quad (1)$$

$$\frac{\partial C_{I,x=L_c}^t}{\partial x} = 0 \quad (2)$$

where $C_{sensor}^t$ may be defined as the concentration of analyte in proximity to the sensor 100 as calculated by the transceiver 101 using the received measurement information from the sensor 100, $C_{I,x=L_c}^t$ may be defined as the concentration of analyte at the interface of the sensor 801 and medium surrounding the sensor, e.g., the interstitial fluid 608, and $L_c$ may be defined as the absolute distance between the sensor 100 and the position in which the concentration of analyte is being calculated, e.g., a capillary 604. However, this is not required, and $L_c$ may be defined as any value that represents some distance over which the concentration of the analyte is being calculated.

In some embodiments, the governing equation may be stored (e.g., in memory 922) and/or solved in a simplified form. The simplified equation may be defined as follows:

$$\frac{\partial C_I(x, t)}{\partial t} = \left(\frac{D_{max} * C_I(x, t)}{K_D + C_I(x, t)}\right)\frac{\partial^2 C_I(x, t)}{\partial x^2} - \frac{V_{max} * C_I(x, t)}{K_m + C_I(x, t)}$$

In these embodiments, $D_{max}$ may represent the maximum attainable diffusivity of the analyte (e.g., in the interstitial fluid space 608), $K_D$ may represent the diffusivity controlling parameter, and $C_I(x, t)$ may represent the concentration of analyte at a given location (x) and time (t), $V_{max}$ may represent the maximum rate of degradation of the analyte (e.g., through the consumption by cells in the interstitial fluid space 608), $K_m$ may represent the degradation rate controlling parameter, and $C_I(x, t)$ may represent the concentration of analyte at a given location (x) and time (t), e.g. in interstitial fluid space 608.

Figure 14:
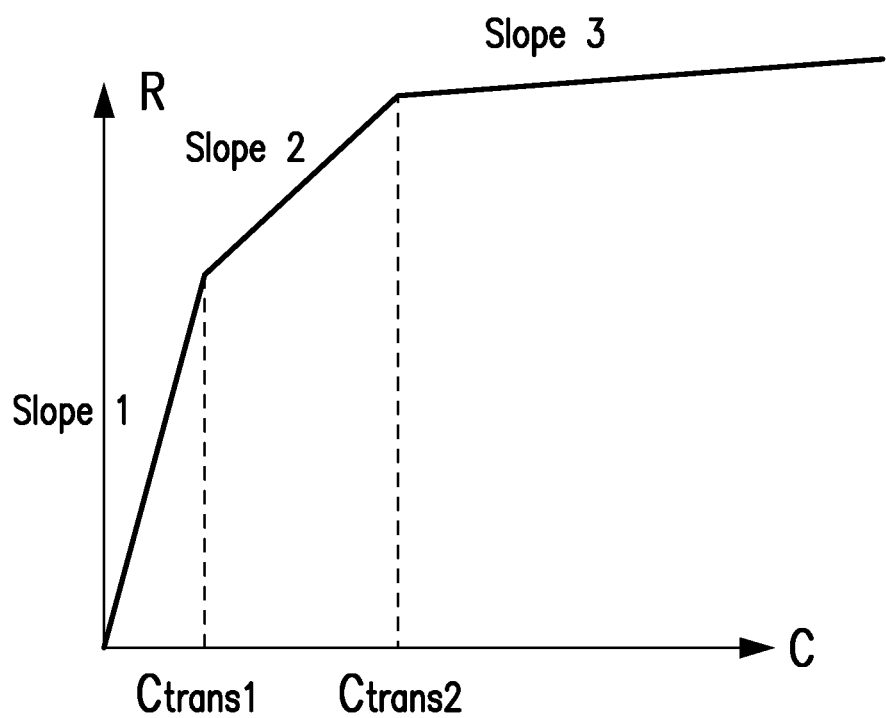
FIG. 14 is a graph illustrating piecewise modeling of analyte degradation over discrete intervals embodying some aspects of the present invention.
Figure 15:
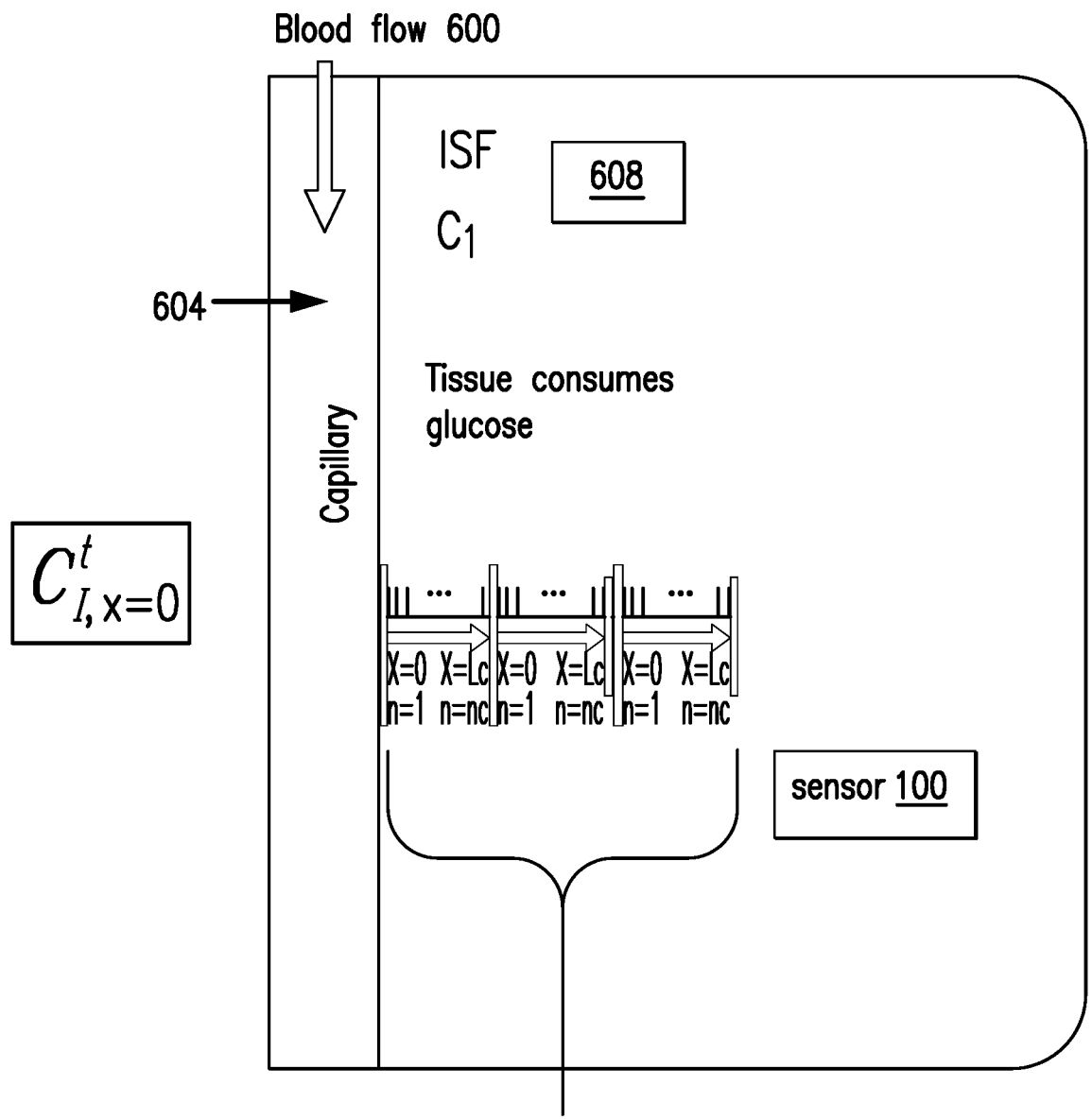
FIG. 15 is a graphical depiction of an exemplary interval over which the concentration of an analyte is modeled in some embodiments of the present invention.

In some embodiments, the governing equation may be stored (e.g., in memory 922) and/or solved in a further simplified form. In some non-limiting embodiments, as shown in FIGS. 14 and 15, the term modeling the degradation of the analyte may be defined piecewise over discrete intervals. In some non-limiting embodiments, the number of intervals may be three, though this is not required, and any number of intervals is acceptable. In some non-limiting embodiments, the governing equation may be defined in the following manner when $C_I(x, t) < C_{trans\_1}$:

$$\frac{\partial C_I(x, t)}{\partial t} = \left(\frac{D_{max} * C_I(x, t)}{K_D + C_I(x, t)}\right)\frac{\partial^2 C_I(x, t)}{\partial x^2} - Slope_1 * C_I(x, t)$$

In these non-limiting embodiments, $C_I(x, t)$ may be defined as the concentration of analyte at a given time and position within the interval over which the analyte monitoring system 50 is performing the calculations. In these non-limiting embodiments, as shown in FIG. 14, $C_{trans\_1}$ may be the upper limit of analyte concentration in the first interval. In some embodiments, $Slope_1$ may be the slope in the first interval (see FIG. 14).

In some non-limiting embodiments, the governing equation may be defined in the following manner when $C_{trans_1} < C(x) < C_{trans_2}$:

$$\frac{\partial C_I(x,t)}{\partial t} = \left(\frac{D_{max} * C_I(x,t)}{K_D + C_I(x,t)}\right)\frac{\partial^2 C_I(x,t)}{\partial x^2} - (Slope_2 * (C_I(x,t) - C_{trans_1}) + R(C_{trans_1}))$$

In these non-limiting embodiments, C(x) may be defined as the concentration of analyte at a given position within the interval over which the analyte monitoring system 50 is performing the calculations. In these non-limiting embodiments, as shown in FIG. 14, $C_{trans_1}$ may be the upper limit of analyte concentration in the first interval, which may also be the lower limit of analyte concentration in the second interval. In some embodiments, $Slope_2$ may be the slope in the second interval, and $C_{trans_2}$ may be the upper limit of analyte concentration in the second interval (see FIG. 14).

In some non-limiting embodiments, the governing equation may be defined in the following manner when $C(x) > C_{trans_2}$:

$$\frac{\partial C_I(x,t)}{\partial t} = \left(\frac{D_{max} * C(x)}{K_D + C(x)}\right)\frac{\partial^2 C(x)}{\partial x^2} - (Slope_3 * (C(x) - C_{trans_2}) + R(C_{trans_2}))$$

In these non-limiting embodiments, C(x) may be defined as the concentration of analyte at a given position within the interval over which the analyte monitoring system 50 is performing the calculations. In these non-limiting embodiments, as shown in FIG. 14, $C_{trans_2}$ may be the upper limit of analyte concentration in the second interval, which may also be the lower limit of analyte concentration in the third interval. In some embodiments, and $Slope_3$ may be the slope in the third interval (see FIG. 14).

In some non-limiting embodiments, the analyte monitoring system 50 may solve for the concentration of the analyte in a medium distant from the sensor 100 (e.g., a capillary 604) by solving the above mentioned governing equation for a specified variable, e.g., $C_{I,x=0}^t$. This may be accomplished in some non-limiting embodiments through discretization of the above mentioned governing equations. In some embodiments, this may be accomplished through an approximation of the partial derivatives utilized in the governing equation over discrete changes in both time and position. This approximation may be accomplished, for example, using a Taylor's series expansion over a discrete number of intervals of fixed width, e.g., over "n" intervals of "Δx" width. However, this is not necessary, and such approximation can be performed over any number of intervals of fixed or varying width of any arbitrary unit. An exemplary discretization is as follows. If the Taylor's series expansion of $C_n^{t+\Delta t}$ is defined as:

$$C_n^{t+\Delta t} = C_n^t + \Delta t\left[\frac{\partial C}{\partial t}\right]_n^t + \frac{\Delta t^2}{2}\left[\frac{\partial^2 C}{\partial t^2}\right]_n^t + O(\Delta t^3)$$

And Δt is assumed to be sufficiently small, then:

$$C_n^{t+\Delta t} \approx C_n^t + \Delta t\left[\frac{\partial C}{\partial t}\right]_n^t$$

Therefore:

$$\left[\frac{\partial C}{\partial t}\right]_n^t \approx \frac{C_n^{t+\Delta t} - C_n^t}{\Delta t}$$

If the Taylor's series expansion of $C_{n+1}^t$ is defined as:

$$C_{n+1}^t = C_n^t + \Delta x\left[\frac{\partial C}{\partial x}\right]_n^t + \frac{\Delta x^2}{2}\left[\frac{\partial^2 C}{\partial x^2}\right]_n^t + O(\Delta x^3)$$

And Δx is assumed to be sufficiently small, then:

$$C_{n+1}^t \approx C_n^t + \Delta x\left[\frac{\partial C}{\partial x}\right]_n^t$$

Therefore:

$$\left[\frac{\partial C}{\partial x}\right]_n^t \approx \frac{C_{n+1}^t - C_n^t}{\Delta x}$$

Taking the derivative of the above expression with respect to x yields:

$$\left[\frac{\partial^2 C}{\partial x^2}\right]_n^t \approx \frac{C_{n+1}^t - 2C_n^t + C_{n-1}^t}{\Delta x^2}$$

In some non-limiting embodiments, the partial derivatives in the discretized governing equation may be replaced by the approximations as obtained through the finite difference method (i.e. through Taylor's series expansion) as shown above.

In some non-limiting embodiments, the PIC controller 920 or other processing element may be configured to use an iterative process to converge a concentration value (e.g. $C_I(x, t-\Delta t)$) to a parameter value (e.g. $\overline{C}(x, t)$).

In some non-limiting embodiments, a processing element, e.g., PIC microcontroller 920, may construct a single column matrix with "n" rows, wherein "n" is the number of discrete intervals created during the discretization process. However, this is not required, and the processing element may use any suitable data architecture to arrive at a numerically solution to the governing equation. This matrix may be stored in local memory of the transceiver, e.g., in memory 922, and may be designated as matrix "b". The first entry of this matrix, i.e. row 1, may be the concentration of the analyte as calculated by transceiver 101 as based upon the measurement data received by sensor 100. In some embodiments, the remaining rows may be populated with variables defined as follows:

$$C_I(n, t-\Delta t) + b_n$$

Where $C_I$ is a calculated concentration of the analyte in the medium surrounding the sensor (i.e., as calculated and modeled through the governing equation), t is a time step, and n is referring to the row of the matrix.

In some non-limiting embodiments, a processing element, e.g., PIC microcontroller 920, may construct a single column matrix with "n" rows, wherein "n" is the number of discrete intervals created during the discretization process. However, this is not required, and the processing element may use any suitable data architecture to arrive at a numerically solution to the governing equation. This matrix may be stored in local memory of the transceiver, e.g., in memory 922, and designated as matrix "x." The rows of matrix "x" may be populated with variables defined as follows:

$$C_f(n,t)$$

Where t is a time step and n is referring to the row of the matrix.

In some non-limiting embodiments, a processing element, e.g., PIC microcontroller 920, may construct a matrix with "n" rows and "n" columns, wherein "n" is the number of discrete intervals created during the discretization process. However, this is not required, and the processing element may use any suitable data architecture to arrive at a numerically solution to the governing equation. This matrix may be stored in local memory of the transceiver, e.g., in memory 922, and designated as matrix "A."

The first row of matrix A may be populated with a null value for column 1 and all remaining columns through column (n−1), and A(1,n)=1. However, this is not required, and the processing element may use any suitable data architecture to arrive at a numerically solution to the governing equation.

In some embodiments, a first entry in each remaining row of matrix A (i.e., those entries comprising row 2 through row n) may be defined with a variable $a_{n,n-1}$ where n is the respective row.

In some embodiments, a second entry in each remaining row of matrix A (i.e., those entries comprising row 2 through row n) may be defined with a variable $a_{n,n}$ where n is the respective row.

In some embodiments, a third entry in the rows of matrix A comprising row 2 through row (n−1) may be defined with a variable $a_{n,n+1}$ where n is the respective row.

In some embodiments, the remaining entries of matrix A may be populated with a null value. However, this is not required, and the processing element may use any suitable data architecture to arrive at a numerically solution to the governing equation.

In some embodiments, the analyte monitoring system 50 may solve for the variables in the "x" matrix through conventional matrix operations. This may be accomplished through the following operation, utilizing the naming convention as described above:

$$x = A'^{*}b$$

Where A' is the inverse of matrix "A" as defined above. However, this is not required, and the analyte monitoring system may utilize any mathematical technique to calculate a solution the governing equation.

In some non-limiting embodiments, the foregoing matrix operations may be performed utilizing conventional functions of the C programming language. However, this is not required, and the analyte monitoring system 50 may utilize any programming language or functions (whether imported or conventional) to perform the calculations to solve the governing equation.

In the embodiments wherein matrix operations are utilized to solve for variables defined in matrix "x" (i.e. $C_f(n,t)$), the value of the variable of row "n" may correspond to $C_{I,x=0}^{t}$, i.e. the desired value of the concentration of the analyte in a distant medium (e.g., a capillary 604). In some embodiments, this value may be stored in the memory of the analyte monitoring system 50, e.g., in memory 922, as $C_{I,x=0}^{t}$. However, this is not required, and the value obtained may be designated as any variable or stored in any suitable memory medium in any suitable data form.

In some embodiments, the transceiver 101 may covey the value obtained for the concentration of the analyte in a distant medium to a display device 105.

From this information, the transmitter 101 may also determine if an alert and/or alarm condition exists, which may be signaled to the user (e.g., through vibration by vibration motor 928 and/or an LED of the transmitter's display 924 and/or a display of a display device 105).

Figure 9:
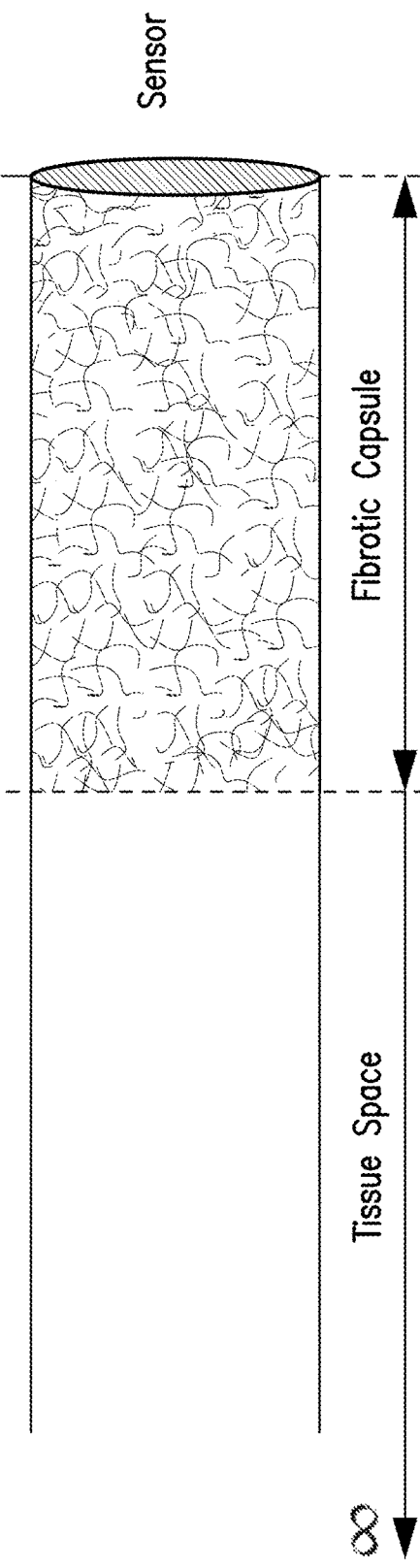
FIG. 9 is a simplified graphical depiction of an exemplary interval over which the concentration of an analyte is modeled in the prior art with exemplary prior art equations and boundary conditions included.

FIGS. 9 and 10 are included to illustrate the advantages that certain embodiments of the current invention possess over the prior art. FIG. 9 represents a graphical depiction of the interval over which the analyte transport is modeled in the prior art (see Novak, supra). Governing equations and boundary conditions in the prior art are included. As can be seen in FIG. 9, the prior art utilizes a two-compartment model with two governing equations—one for each compartment—that must be solved simultaneously to achieve a solution. In order to accommodate the increased complexity introduced by multiple governing equations, four boundary conditions are necessary to numerically solve for a solution. This increased complexity requires additional computing power and is more difficult to implement in a real-time system, as compared to embodiments of the present invention (compare FIG. 8).

FIG. 10 is a chart summarizing and contrasting the boundary conditions necessary to model the transport of an analyte across a medium surrounding a sensor in the prior art (Novak, supra) and in a non-limiting embodiment of the present invention. In the prior art, the boundary conditions are defined as the distance from the sensor approaches infinity, at the tissue/capsule interface, and at the sensor interface. Because two governing equations are needed to model the transport of the analyte across two compartments used conventionally, four total boundary conditions are necessary. In a non-limiting embodiment of the present invention, only two boundary conditions are necessary to solve the single governing equation. Additionally, the boundary conditions are defined over a discrete interval. As shown in FIG. 10, in this embodiment, the boundary conditions are much simpler in terms of the number of variables utilized and the number of boundary conditions necessary. This simplicity may make embodiments of the present invention suitable for use in a real-time system.

Figure 11:
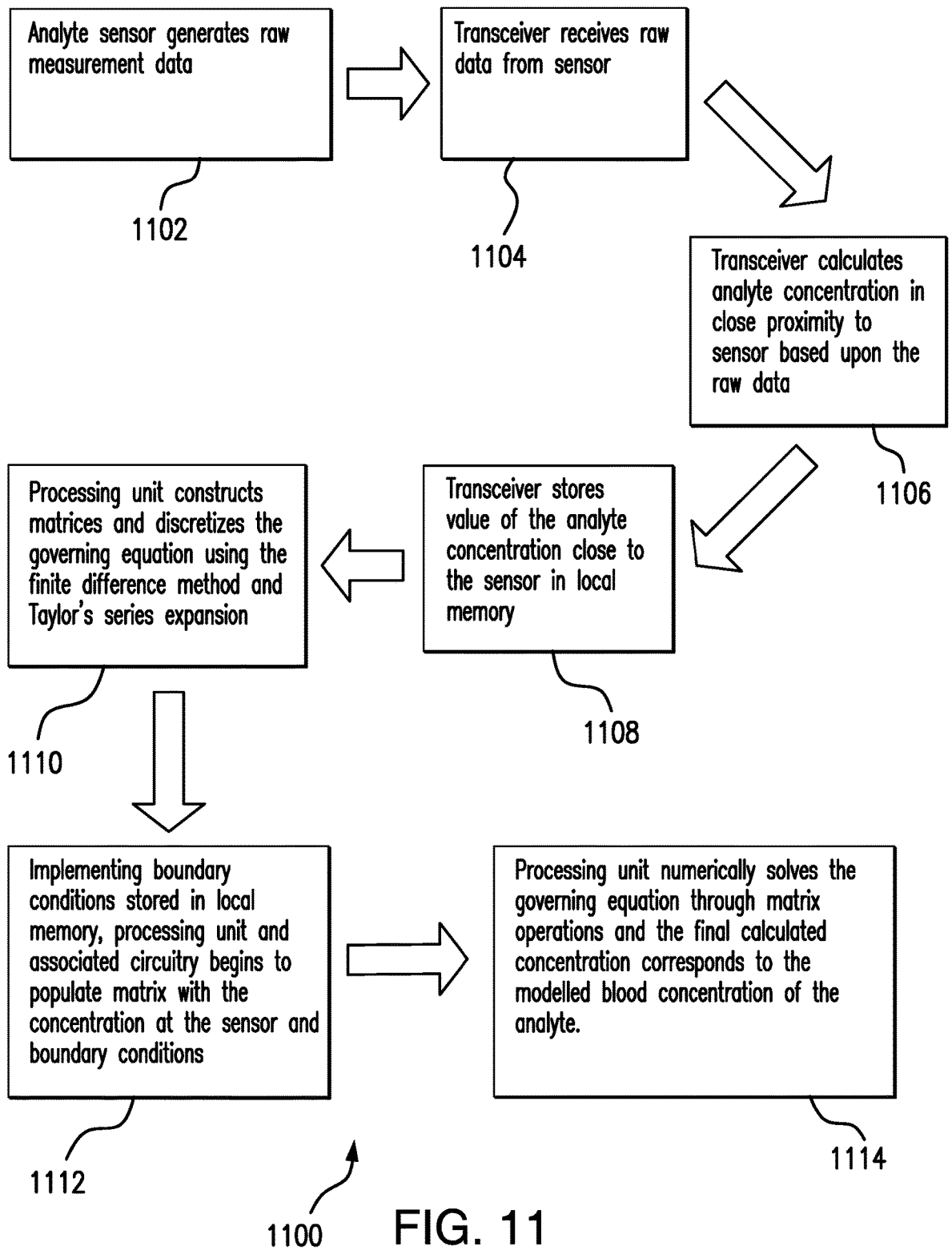
FIG. 11 is a flow chart illustrating a process for predicting the concentration of an analyte in a medium located away from the sensor embodying aspects of the present invention.

FIG. 11 is a flow chart illustrating a process 1100 for calculating the concentration of analyte in a distant medium, e.g. a capillary 604, according to some embodiments that utilize an analyte transport model. In some embodiments, the transceiver 101 of analyte monitoring system 50 performs one or more steps of the analyte concentration calculation process 1100. In some embodiments, the process 1100 may begin in step 1102 with an analyte sensor 100 generating raw measurement data based on one or more detectable properties exhibited by the analyte in close proximity to the sensor 100. The process 1100 may also include a step 1104 wherein the transceiver 101 receives the raw data from the sensor 100. The process 1100 may also include a step 1106 wherein the transceiver 101 calculates the concentration of the analyte in close proximity to the sensor 100 based on at least the raw measurement data received from the sensor 100. The process 1100 may also include a step 1108 wherein the transceiver 101 stores the calculated value of the analyte concentration in close proximity to the sensor 100 in local memory, e.g. in memory 922.

The process 1100 may then continue with a processing unit, e.g. PIC microcontroller 920, assembling a suitable data architecture to solve a pre-programmed governing equation that describes the transport of the analyte through a medium surrounding the sensor 100, e.g. interstitial fluid space 608. In some non-limiting embodiments, as described by step 1110, this governing equation may be discretized and simplified through suitable and conventional mathematic techniques known in the art, e.g. a Taylor's series expansion and finite difference method. In some non-limiting embodiments, the processing unit may assemble a matrix containing at least the calculated concentration value of the analyte in close proximity to the sensor 100. However, this is not required, and any suitable data architecture to arrive at a solution to the governing equation may be utilized.

The process 1100 may continue with step 1112 wherein the boundary conditions stored in local memory, e.g. memory 922, may be utilized to populate additional matrices by a processing unit, e.g. PIC controller 920, and other associated circuitry. However, this is not required, and any suitable data architecture in which the governing equation may be solved may be utilized.

The process 1100 may continue a step 1114 wherein a processing unit, e.g. PIC controller 920, numerically solves the governing equation utilizing the calculated value of the analyte in close proximity to the sensor 100 and the programmed boundary conditions and parameters. In some embodiments, this calculation may be completed utilizing matrix operations and the assembled matrices of steps 1110 and 1112.

The process 1100 may contain additional steps and the steps described above are meant to be illustrative and not exhaustive. For example, the process may continue with the calculated analyte concentration value in the distant medium obtained through solving the governing equation being stored in local memory, e.g. memory 922, or displayed on display device 105. In some non-limiting embodiments, the solving the governing equation may include using a lookup table or coefficients of a polynomial stored in local memory (e.g., memory 922).

Figure 12:
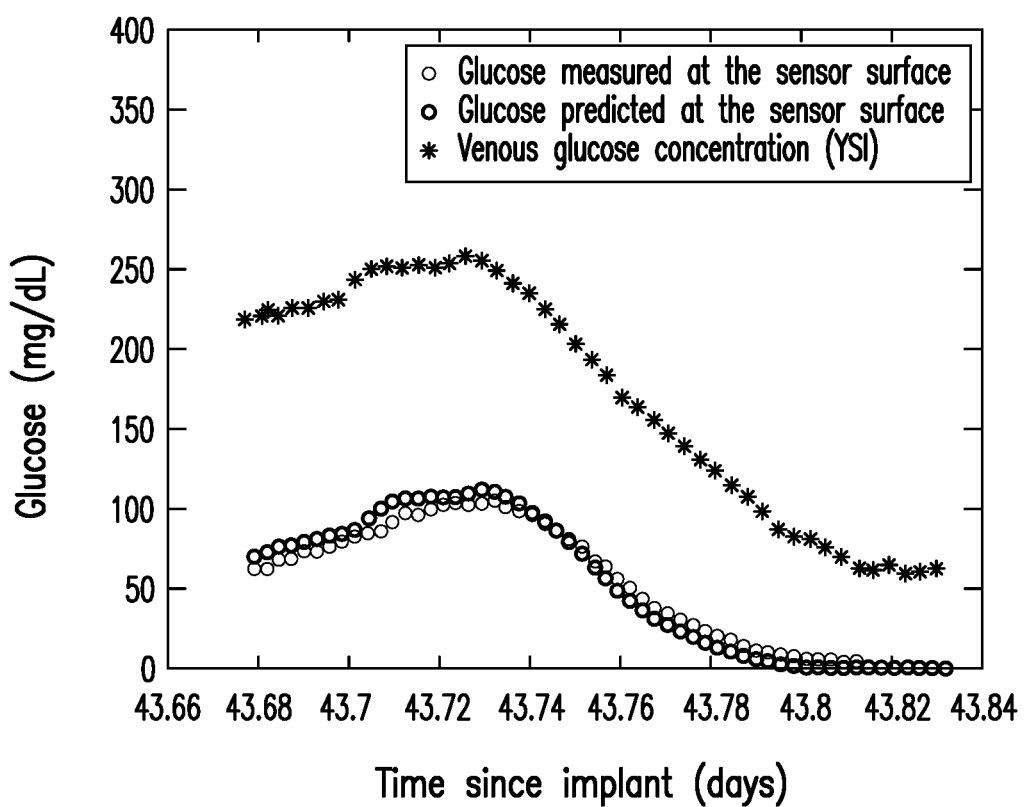
FIG. 12 is a graph displaying a non-limiting example of data verifying the model as carried out by a non-limiting embodiment of the present invention.

FIG. 12 is a graph illustrating a model verification of one embodiment of the present invention, measured approximately 43 days after the implant of a sensor. As the graph illustrates, the model closely predicts and tracks the analyte concentration as measured on the sensor surface.

Figure 13:
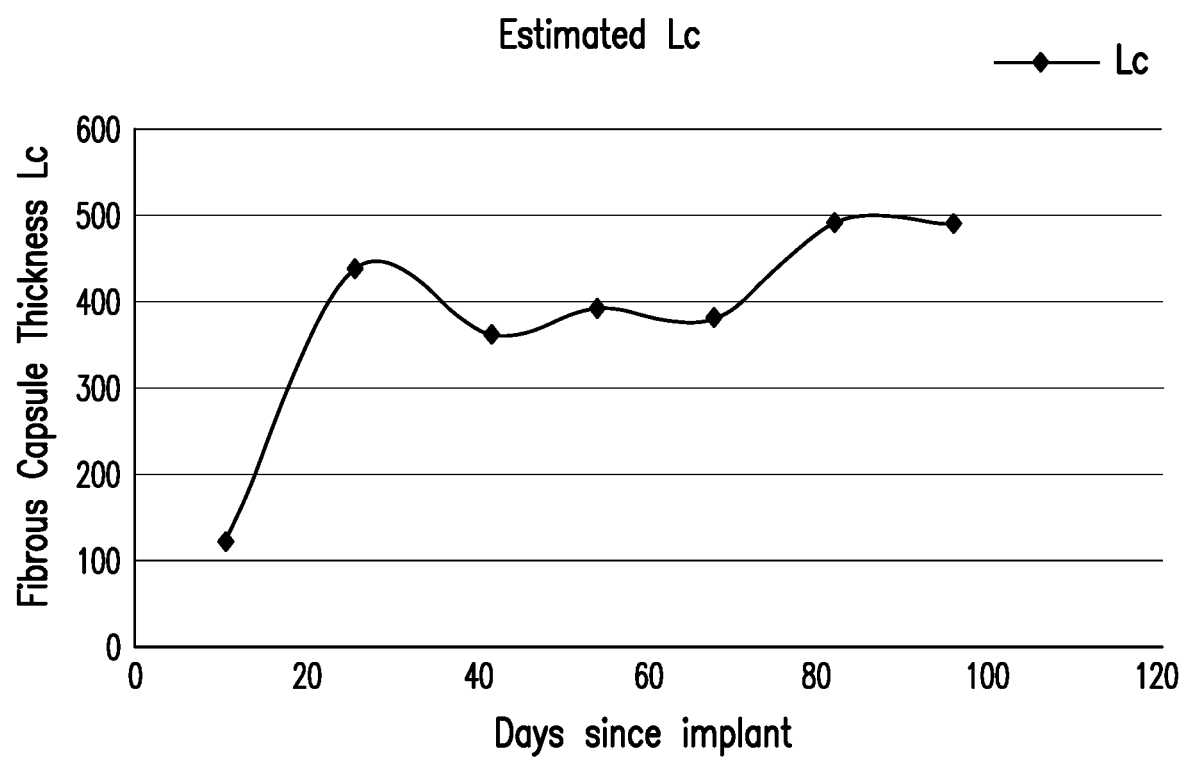
FIG. 13 is a graph displaying an estimated thickness of a fibrous capsule surrounding an implanted sensor exemplary of a non-limiting embodiment of the present invention.

FIG. 13 is a graph illustrating the length of a fibrous capsule surrounding a sensor. In some non-limiting embodiments, FIG. 13 may show the length of the fibrous capsule in units of micrometers. The length is estimated over a period of approximately 100 days following the implantation of the sensor. As shown by the data, the fibrous capsule grows quickly over the first 20 days. The capsule length then decreases slightly until approximately day 40 and then remains fairly constant until day 70. The length of the capsule increases until day 80, and then remains fairly constant until day 100.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For instance, although aspects of the invention have been described above with modeling the transport of analyte (e.g., glucose) through a medium surrounding an implanted analyte sensor, in some alternative embodiments, the transport model of the present invention may be applied to different devices (e.g., a temperature sensor, an insulin pump, or a pacemaker) in different systems (e.g., temperature monitoring systems, insulin delivery systems, or cardiac contraction control systems). Also, although examples of particular parameters, thresholds, and time periods used in the transport of the analyte through a medium surrounding an implanted system have been described above, the parameters, thresholds, and time periods may vary from one embodiment to the next, and different parameters, thresholds, and time periods may be used for different sensors and/or system configurations.

In addition, although in some embodiments the transceiver 101 of the analyte monitoring system 50 performs one or more of the calculation of analyte in proximity to the sensor 100, analyte transport calculation based upon the programmed equations, boundary conditions, and parameters, and calculation and conveyance of a calculated analyte concentration in a distant medium, this is not required. In some alternative embodiments, portions of or all of the calculation of analyte in proximity to the sensor 100, analyte transport calculation based upon the programmed equations, boundary conditions, and parameters, and calculation and conveyance of a calculated analyte concentration in a distant medium, this is not required and may be performed by one or more of the analyte sensor 100 and display device 105.

What is claimed is:

1. An analyte monitoring system comprising:
   an analyte sensor including an indicator element that exhibits one or more detectable properties based on a concentration of an analyte in proximity to the indicator element; and
   a transceiver configured to (i) receive measurement information from the analyte sensor, (ii) calculate the concentration of the analyte in proximity to the indicator element based on at least the received measurement information, and (iii) calculate a blood analyte concentration based on the calculated concentration of the analyte in proximity to the indicator element by (1) incorporating the calculated concentration of the analyte in proximity to the indicator element into a governing equation that models analyte transport over an interval, and (2) solving the governing equation;
   wherein the governing equation includes no more than two discrete boundary conditions, and the interval has a first endpoint at an interface between a bloodstream and surrounding tissue and a second endpoint at the sensor.

2. The analyte monitoring system of claim 1, wherein the two discrete boundary conditions include (1) a concentration of the analyte at the second endpoint being equal to the calculated concentration of the analyte in proximity to the indicator element, and (2) constant flux of the analyte at the second endpoint.

3. The analyte monitoring system of claim 1, wherein the governing equation includes a parameter for a maximum attainable diffusivity of the analyte and a diffusivity controlling parameter.

4. The analyte monitoring system of claim 1, wherein the governing equation relates a rate of change of the concentration of the analyte over time to a diffusivity of the analyte at a given location within the interval.

5. The analyte monitoring system of claim 1, wherein the transceiver is configured to calculate the blood analyte concentration in real time, based on at least the calculated analyte concentration in proximity to the sensor.

6. The analyte monitoring system of claim 1, wherein the medium surrounding the sensor is a fibrous capsule.

7. An analyte monitoring system comprising:
an analyte sensor including an indicator element that exhibits one or more detectable properties based on a concentration of an analyte in proximity to the indicator element; and
a transceiver configured to (i) receive measurement information from the analyte sensor, (ii) calculate the concentration of the analyte in proximity to the indicator element based on at least the received measurement information, and (iii) calculate a blood analyte concentration based on the calculated concentration of the analyte in proximity to the indicator element by (1) incorporating the calculated concentration of the analyte in proximity to the indicator element into a governing equation that models analyte transport over an interval, and (2) solving the governing equation;
wherein the governing equation includes no more than two discrete boundary conditions, and the governing equation and the boundary conditions are defined in the Cartesian coordinate system.

8. An analyte monitoring system comprising:
an analyte sensor including an indicator element that exhibits one or more detectable properties based on a concentration of an analyte in proximity to the indicator element and
a transceiver configured to (i) receive measurement information from the analyte sensor, (ii) calculate the concentration of the analyte in proximity to the indicator element based on at least the received measurement information, and (iii) calculate a blood analyte concentration based on the calculated concentration of the analyte in proximity to the indicator element by (1) incorporating the calculated concentration of the analyte in proximity to the indicator element into a governing equation that models analyte transport over an interval, and (2) solving the governing equation;
wherein the governing equation includes no more than two discrete boundary conditions, the governing equation accounts for consumption of the analyte, and the governing equation includes a maximum rate of consumption parameter.

9. The analyte monitoring system of claim 8, wherein the interval has a first endpoint at an interface between a bloodstream and surrounding tissue and a second endpoint at the sensor.

10. The analyte monitoring system of claim 8, wherein the governing equation includes a consumption rate controlling parameter.

11. The analyte monitoring system of claim 8, wherein the governing equation accounts for consumption of the analyte using a Michaelis-Menten equation, and the consumption is defined in the Cartesian coordinate system.

12. An analyte monitoring system comprising:
an analyte sensor including an indicator element that exhibits one or more detectable properties based on a concentration of an analyte in proximity to the indicator element and
a transceiver configured to (i) receive measurement information from the analyte sensor, (ii) calculate the concentration of the analyte in proximity to the indicator element based on at least the received measurement information, and (iii) calculate a blood analyte concentration based on the calculated concentration of the analyte in proximity to the indicator element by (1) incorporating the calculated concentration of the analyte in proximity to the indicator element into a governing equation that models analyte transport over an interval, and (2) solving the governing equation;
wherein the governing equation includes no more than two discrete boundary conditions, and the transceiver is further configured to solve the governing equation numerically using a discretization process followed by a linear algebra process.

13. The analyte monitoring system of claim 12, wherein the transceiver is configured to perform the discretization process using a finite difference method.

* * * * *